(12) United States Patent
Stouffer

(10) Patent No.: US 10,342,984 B2
(45) Date of Patent: Jul. 9, 2019

(54) SPLIT COIL FOR UNIFORM MAGNETIC FIELD GENERATION FROM AN EXTERNAL CHARGER FOR AN IMPLANTABLE MEDICAL DEVICE

(71) Applicant: Boston Scientific Neuromodulation Corporation, Valencia, CA (US)

(72) Inventor: Thomas W. Stouffer, Chatsworth, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 154 days.

(21) Appl. No.: 15/616,402

(22) Filed: Jun. 7, 2017

(65) Prior Publication Data

US 2017/0361111 A1 Dec. 21, 2017

Related U.S. Application Data

(60) Provisional application No. 62/350,511, filed on Jun. 15, 2016.

(51) Int. Cl.
| | |
|---|---|
| *H02J 7/00* | (2006.01) |
| *H02J 7/04* | (2006.01) |
| *A61N 1/378* | (2006.01) |
| *H02J 50/90* | (2016.01) |
| *H02J 50/10* | (2016.01) |
| *A61N 1/36* | (2006.01) |
| *A61N 1/372* | (2006.01) |
| *H01F 27/28* | (2006.01) |

(Continued)

(52) U.S. Cl.
CPC ....... *A61N 1/3787* (2013.01); *A61N 1/36125* (2013.01); *A61N 1/36142* (2013.01); *A61N 1/37229* (2013.01); *H01F 27/2804* (2013.01); *H01F 38/14* (2013.01); *H02J 7/025* (2013.01);
(Continued)

(58) Field of Classification Search
USPC ................. 320/108, 107, 109, 101
See application file for complete search history.

(56) References Cited

U.S. PATENT DOCUMENTS

| 4,550,731 A | 11/1985 | Batina et al. |
|---|---|---|
| 5,314,453 A | 5/1994 | Jeutter |

(Continued)

FOREIGN PATENT DOCUMENTS

| DE | 19909479 | 8/2000 |
|---|---|---|
| DE | 10046027 | 3/2002 |

(Continued)

OTHER PUBLICATIONS

US 9,601,939 B2, 03/2017, Cong et al. (withdrawn)
(Continued)

*Primary Examiner* — Alexis B Pacheco
(74) *Attorney, Agent, or Firm* — Lewis & Reese, PLLC

(57) ABSTRACT

A charging system for an Implantable Medical Device (IMD) includes a split charging coil for generating a magnetic field to provide power to the IMD. The split charging coil includes a first coil portion and a second coil portion, each of which can be formed as a mechanical winding of an insulated conductor. The first and second coil portions are connected to each other in a way that substantially reduces or eliminates any current-carrying path that is routed radially with respect to the coil. As a result, the split coil produces a uniform magnetic field that enables a more accurate determination of alignment between the coil and the IMD than is available using traditional charging coils.

20 Claims, 11 Drawing Sheets

(51) Int. Cl.
*H01F 38/14* (2006.01)
*H02J 7/02* (2016.01)
*A61N 1/05* (2006.01)

(52) U.S. Cl.
CPC .............. *H02J 50/10* (2016.02); *H02J 50/90* (2016.02); *A61N 1/0534* (2013.01); *A61N 1/0551* (2013.01)

(56) References Cited

U.S. PATENT DOCUMENTS

| | | | |
|---|---|---|---|
| 5,591,217 A | 1/1997 | Barreras | |
| 5,690,693 A | 11/1997 | Wang et al. | |
| 5,704,352 A | 1/1998 | Tremblay et al. | |
| 5,749,909 A | 5/1998 | Schroeppel et al. | |
| 5,769,877 A | 6/1998 | Barreras, Sr. | |
| 5,807,397 A | 9/1998 | Barreras | |
| 5,948,006 A | 9/1999 | Mann | |
| 5,973,611 A | 10/1999 | Kulha et al. | |
| 5,991,665 A | 11/1999 | Wang et al. | |
| 6,009,878 A | 1/2000 | Weijand et al. | |
| 6,047,214 A | 4/2000 | Mueller et al. | |
| 6,138,681 A | 10/2000 | Chen et al. | |
| 6,212,430 B1 | 4/2001 | Kung | |
| 6,275,737 B1 | 8/2001 | Mann | |
| 6,298,271 B1 | 10/2001 | Weijand | |
| 6,430,444 B1 | 8/2002 | Borza | |
| 6,510,345 B1 | 1/2003 | Van Bentem | |
| 6,516,227 B1 | 2/2003 | Meadows et al. | |
| 6,553,263 B1 | 4/2003 | Meadows et al. | |
| 7,167,756 B1 | 1/2007 | Torgerson et al. | |
| 7,177,690 B2 | 2/2007 | Woods et al. | |
| 7,177,698 B2 | 2/2007 | Klosterman et al. | |
| 7,191,013 B1 | 3/2007 | Miranda et al. | |
| 7,225,032 B2 | 5/2007 | Schmeling et al. | |
| 7,286,880 B2 | 10/2007 | Olson et al. | |
| 7,505,816 B2 | 3/2009 | Schmeling et al. | |
| 7,650,192 B2 | 1/2010 | Wahlstrand | |
| 7,774,069 B2 | 8/2010 | Olson et al. | |
| 7,932,696 B2 | 4/2011 | Peterson | |
| 8,005,547 B2 | 8/2011 | Forsberg et al. | |
| 8,140,168 B2 | 3/2012 | Olson et al. | |
| 8,214,042 B2 | 7/2012 | Ozawa et al. | |
| 8,229,567 B2 | 7/2012 | Phillips et al. | |
| 8,260,432 B2 | 9/2012 | DiGiore et al. | |
| 8,311,638 B2 | 11/2012 | Aghassian | |
| 8,321,027 B2 | 11/2012 | Mozzi et al. | |
| 8,321,029 B2 | 11/2012 | Aghassian | |
| 8,335,569 B2 | 12/2012 | Aghassian | |
| 8,346,361 B2 | 1/2013 | Bauhahn et al. | |
| 8,362,742 B2 | 1/2013 | Kallmyer | |
| 8,401,663 B2 | 3/2013 | Aghassian | |
| 8,401,664 B2 | 3/2013 | Chow et al. | |
| 8,473,066 B2 | 6/2013 | Aghassian et al. | |
| 8,498,716 B2 | 7/2013 | Chen et al. | |
| 8,509,912 B2 | 8/2013 | Morgan et al. | |
| 8,554,322 B2 | 10/2013 | Olson et al. | |
| 8,577,474 B2 * | 11/2013 | Rahman | A61N 1/3718 607/60 |
| 8,608,635 B2 | 12/2013 | Yomtov et al. | |
| 8,612,013 B2 | 12/2013 | Forsell | |
| 8,626,297 B2 | 1/2014 | Jaax et al. | |
| 8,666,491 B2 | 3/2014 | Chen et al. | |
| 8,682,444 B2 | 3/2014 | Aghassian et al. | |
| 8,712,541 B2 | 4/2014 | Olson et al. | |
| 8,744,592 B2 | 6/2014 | Carbunaru et al. | |
| 8,751,001 B2 | 6/2014 | Grevious et al. | |
| 8,831,730 B2 | 9/2014 | Mashiach et al. | |
| 8,886,333 B2 | 11/2014 | Lui et al. | |
| 8,901,878 B2 | 12/2014 | Prutchi et al. | |
| 8,942,935 B2 | 1/2015 | Michaels et al. | |
| 9,002,445 B2 | 4/2015 | Chen | |
| 9,030,159 B2 | 5/2015 | Chen et al. | |
| 9,031,665 B2 | 5/2015 | Aghassian | |
| 9,031,666 B2 | 5/2015 | Fell | |
| 9,101,768 B2 | 8/2015 | Khalil et al. | |
| 9,142,989 B2 | 9/2015 | Fell et al. | |
| 9,155,900 B2 | 10/2015 | Meskens | |
| 9,186,520 B2 | 11/2015 | Aghassian | |
| 9,209,634 B2 | 12/2015 | Cottrill et al. | |
| 9,211,418 B2 | 12/2015 | Aghassian | |
| 9,227,075 B2 | 1/2016 | Aghassian et al. | |
| 9,259,584 B2 | 2/2016 | Bauhahn et al. | |
| 9,314,642 B2 | 4/2016 | Ozawa et al. | |
| 9,339,660 B2 | 5/2016 | Feldman et al. | |
| 9,345,883 B2 * | 5/2016 | Marnfeldt | A61N 1/36125 |
| 9,498,635 B2 | 11/2016 | Dellamano et al. | |
| 9,577,714 B2 | 2/2017 | Rehm | |
| 2002/0055763 A1 | 5/2002 | Zarinetchi et al. | |
| 2003/0085684 A1 | 5/2003 | Tsukamoto et al. | |
| 2003/0114899 A1 | 6/2003 | Woods et al. | |
| 2004/0106963 A1 | 6/2004 | Tsukamoto et al. | |
| 2004/0230247 A1 | 11/2004 | Stein et al. | |
| 2005/0131486 A1 | 6/2005 | Boveja et al. | |
| 2006/0227989 A1 | 10/2006 | Polinske | |
| 2007/0060980 A1 | 3/2007 | Strother et al. | |
| 2007/0103617 A1 | 5/2007 | Kitajima et al. | |
| 2007/0129767 A1 | 6/2007 | Wahlstrand | |
| 2008/0027293 A1 | 1/2008 | Vodermayer et al. | |
| 2008/0027513 A1 | 1/2008 | Carbunaru | |
| 2008/0046034 A1 | 2/2008 | Ibrahim | |
| 2008/0172109 A1 * | 7/2008 | Rahman | A61N 1/37229 607/60 |
| 2008/0312530 A1 | 12/2008 | Malackowski et al. | |
| 2009/0069869 A1 | 3/2009 | Stouffer et al. | |
| 2009/0082835 A1 | 3/2009 | Jaax et al. | |
| 2009/0112291 A1 | 4/2009 | Wahlstrand et al. | |
| 2009/0118796 A1 | 5/2009 | Chen et al. | |
| 2009/0216068 A1 | 8/2009 | Thomas et al. | |
| 2010/0331917 A1 | 12/2010 | DiGiore et al. | |
| 2010/0331918 A1 | 12/2010 | DiGiore et al. | |
| 2010/0331919 A1 | 12/2010 | DiGiore et al. | |
| 2011/0004278 A1 | 1/2011 | Aghassian et al. | |
| 2011/0276111 A1 | 11/2011 | Carbunaru et al. | |
| 2011/0301667 A1 | 12/2011 | Olson et al. | |
| 2012/0012630 A1 | 1/2012 | Lui et al. | |
| 2012/0262108 A1 | 10/2012 | Olson et al. | |
| 2012/0277831 A1 | 11/2012 | Joshi | |
| 2012/0319647 A1 * | 12/2012 | Itabashi | H02M 3/33553 320/108 |
| 2013/0009665 A1 | 1/2013 | Clerc et al. | |
| 2013/0023958 A1 | 1/2013 | Fell | |
| 2013/0096651 A1 | 4/2013 | Ozawa et al. | |
| 2013/0197608 A1 | 8/2013 | Eiger | |
| 2014/0084862 A1 * | 3/2014 | Kawaguchi | B60L 11/005 320/108 |
| 2014/0114373 A1 | 4/2014 | Aghassian | |
| 2014/0266019 A1 | 9/2014 | Pigott | |
| 2014/0324126 A1 | 10/2014 | Ozawa | |
| 2014/0354211 A1 | 12/2014 | Zottola et al. | |
| 2015/0028798 A1 | 1/2015 | Dearden et al. | |
| 2015/0360038 A1 | 12/2015 | Zottola et al. | |
| 2016/0096028 A1 | 4/2016 | Aghassian | |
| 2016/0118806 A1 | 4/2016 | Standke et al. | |
| 2016/0126771 A1 * | 5/2016 | Aghassian | H02J 7/025 320/108 |
| 2016/0263385 A1 | 9/2016 | Aghassian | |
| 2016/0301239 A1 | 10/2016 | Funderburk | |
| 2016/0367822 A1 | 12/2016 | Parramon | |
| 2017/0053737 A1 * | 2/2017 | Kurs | H03H 7/40 |
| 2017/0151440 A1 | 6/2017 | Parramon et al. | |
| 2018/0345025 A1 * | 12/2018 | Stinauer | A61N 1/3787 |

FOREIGN PATENT DOCUMENTS

| | | |
|---|---|---|
| EP | 0419729 | 4/1991 |
| EP | 2451526 | 6/2013 |
| WO | 2004/021876 | 3/2004 |

OTHER PUBLICATIONS

U.S. Appl. No. 62/286,253, Howard, filed Jan. 22, 2016.
U.S. Appl. No. 62/286,257, Howard, filed Jan. 22, 2016.

(56) References Cited

OTHER PUBLICATIONS

J. Miller et al., "Development of an Autotuned Transcutaneous Energy Transfer System," J. American Soc'y for Artificial Internal Organs (ASAIO), pp. M706-710 (1993).
Mitamura, Yoshinori, et al., "A Transcutaneous Optical Information Transmission System for Implantable Motor-Driven Artificial Hearts," ASAIO Transactions, Bd. 36, Jul. 1, 1990, pp. 278-280.
Okamoto, Eiji, et al., "Development of a Bidirectional Transcutaneous Optical Data Transmission System for Artificial Hearts Allowing Long-Distance Data Communication with Low Electric Power Consumption," Journal of Artificial Organs—The Official Journal of the Japanese Society for Artificial Organs, Springer-Verlag, TO, Bd. 8, Nr. 3, Sep. 1, 2005, pp. 5 pages.
International Search Report and Written Opinion regarding PCT Application No. PCT/US2017/036827, dated Sep. 27, 2017.

\* cited by examiner

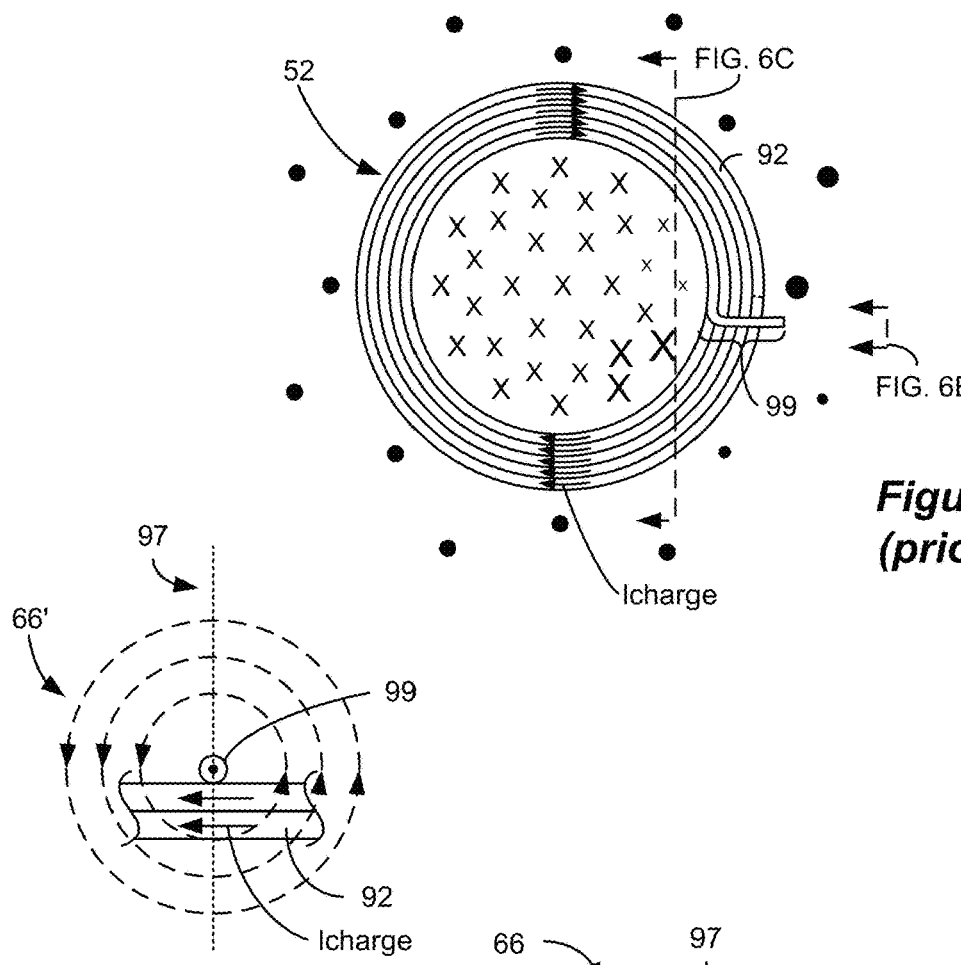
*Figure 6A (prior art)*
*Figure 6B (prior art)*
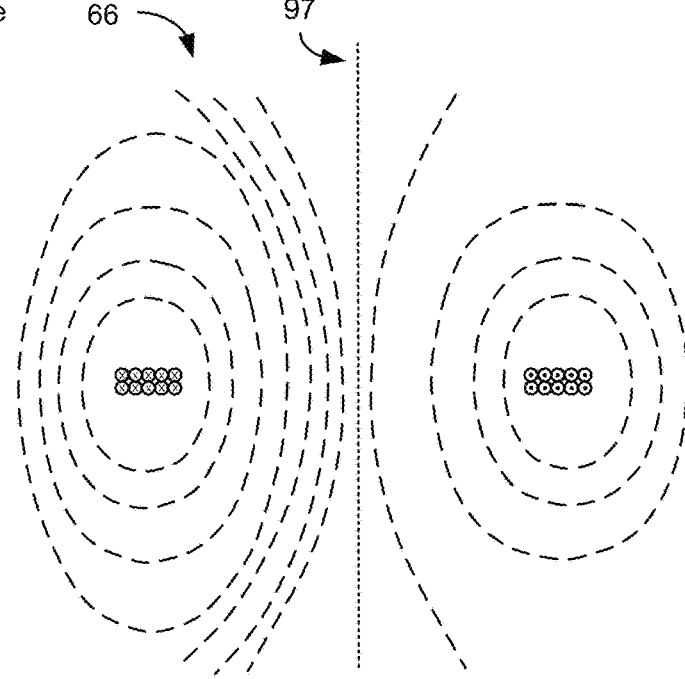
*Figure 6C (prior art)*

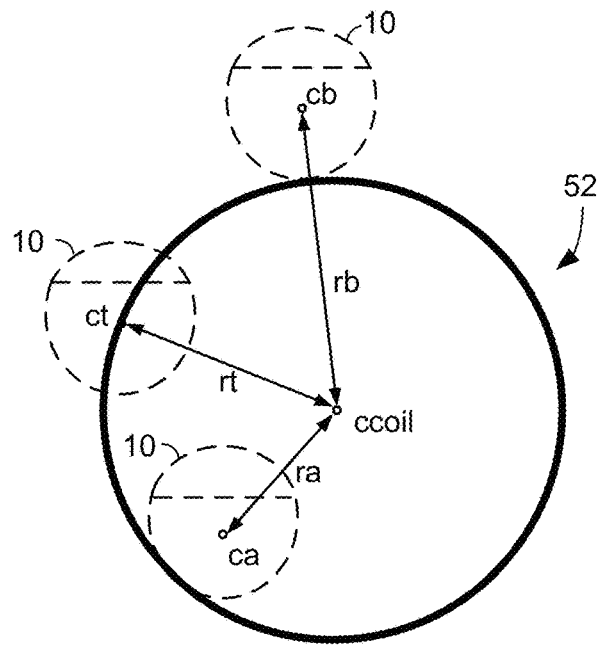
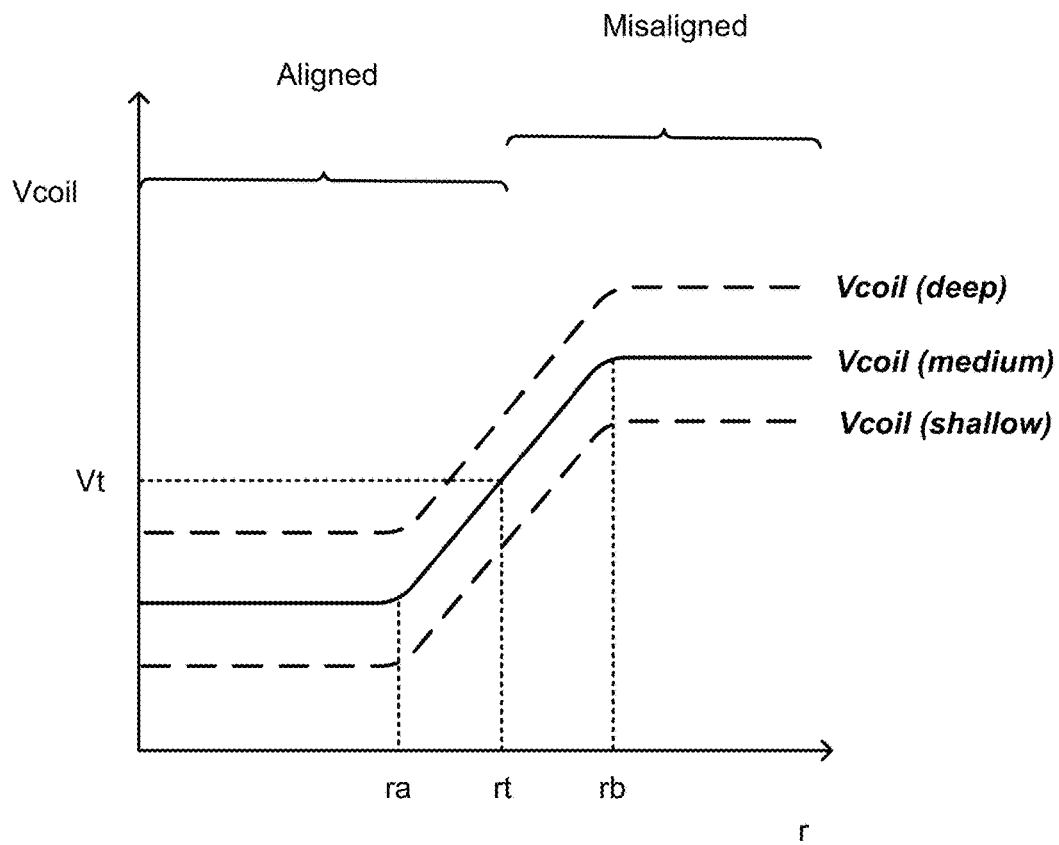
*Figure 7*
*(prior art)*

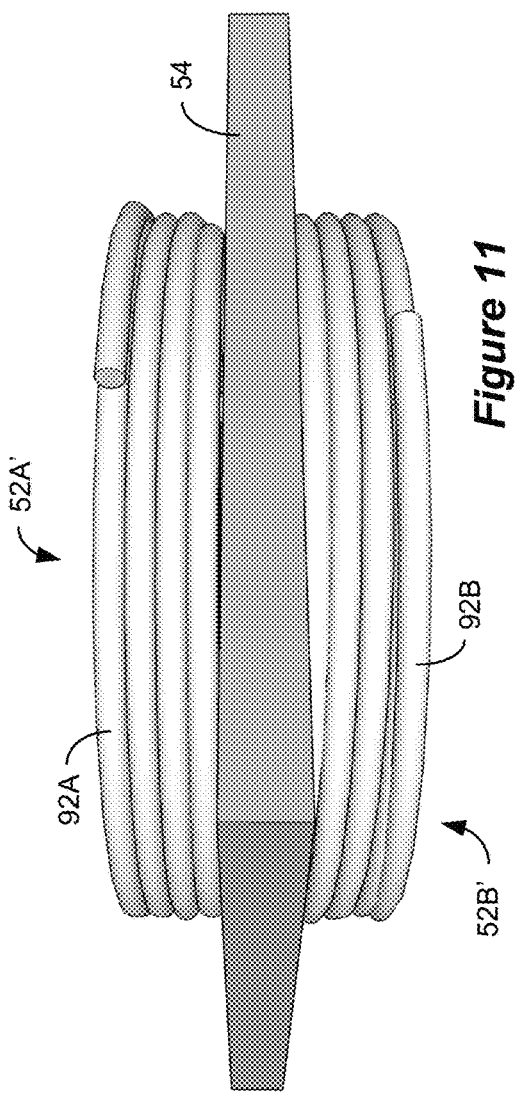
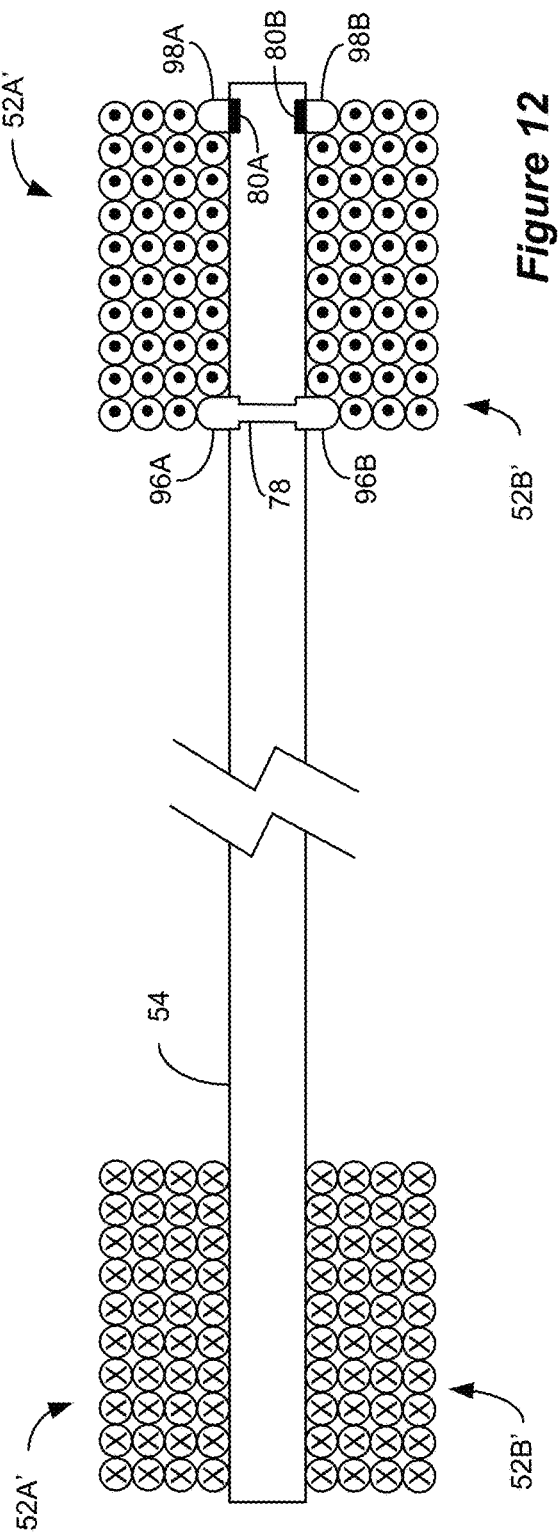

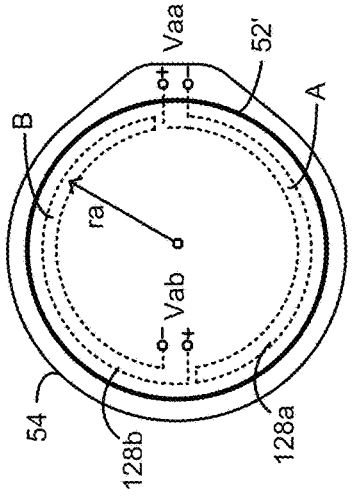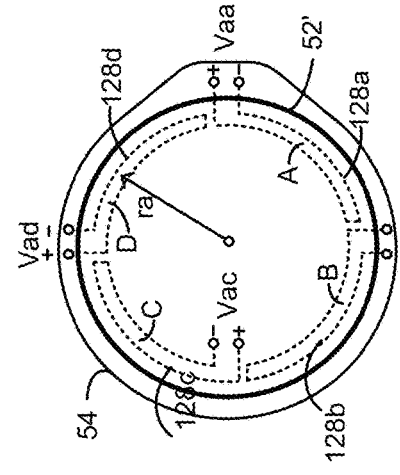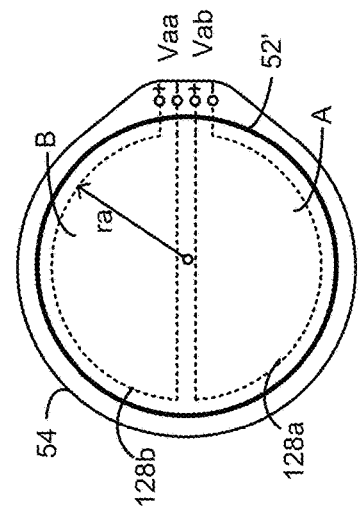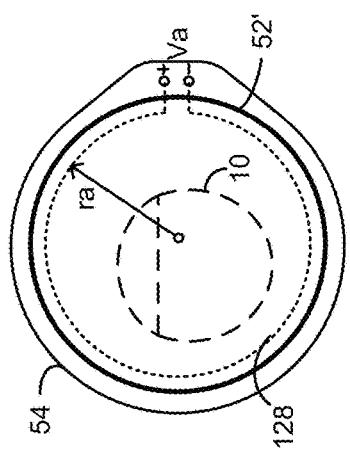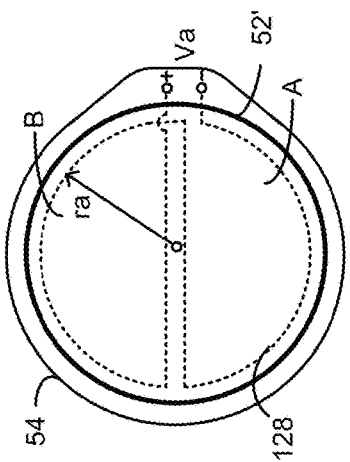

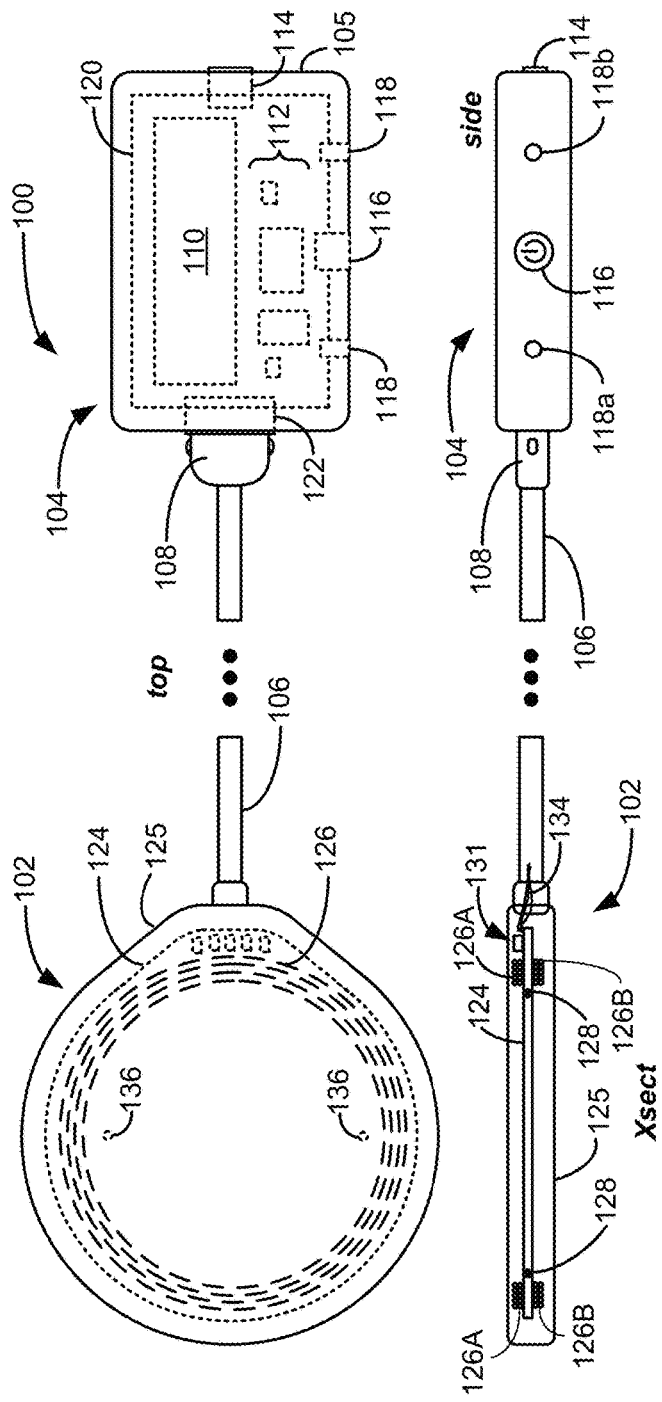
*Figure 14A*
*Figure 14B*
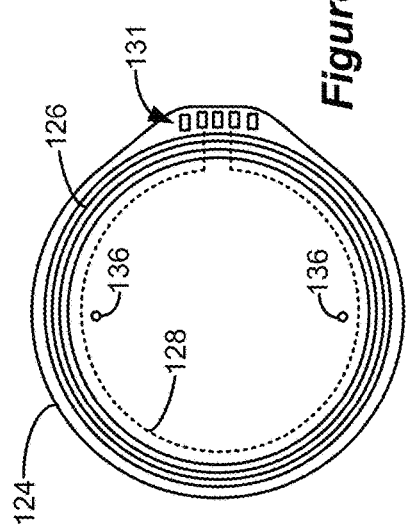
*Figure 14C*

SPLIT COIL FOR UNIFORM MAGNETIC FIELD GENERATION FROM AN EXTERNAL CHARGER FOR AN IMPLANTABLE MEDICAL DEVICE

CROSS-REFERENCE TO RELATED APPLICATIONS

This is a non-provisional of U.S. Provisional Patent Application Ser. No. 62/350,511, filed Jun. 15, 2016, to which priority is claimed, and which is incorporated herein by reference in its entirety.

FIELD OF THE INVENTION

The present invention relates to wireless external chargers for use in implantable medical device systems.

BACKGROUND

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability in any implantable medical device system.

As shown in FIGS. 1A-1C, a SCS system typically includes an Implantable Pulse Generator (IPG) 10 (Implantable Medical Device (IMD) 10 more generally), which includes a biocompatible device case 12 formed of a conductive material such as titanium for example. The case 12 typically holds the circuitry and battery 14 (FIG. 1C) necessary for the IMD 10 to function, although IMDs can also be powered via external RF energy and without a battery. The IMD 10 is coupled to electrodes 16 via one or more electrode leads 18, such that the electrodes 16 form an electrode array 20. The electrodes 16 are carried on a flexible body 22, which also houses the individual signal wires 24 coupled to each electrode. In the illustrated embodiment, there are eight electrodes (Ex) on each lead 18, although the number of leads and electrodes is application specific and therefore can vary. The leads 18 couple to the IMD 10 using lead connectors 26, which are fixed in a non-conductive header material 28, which can comprise an epoxy for example.

As shown in the cross-section of FIG. 1C, the IMD 10 typically includes a printed circuit board (PCB) 30, along with various electronic components 32 mounted to the PCB 30. Two coils (more generally, antennas) are shown in the IMD 10: a telemetry coil 34 used to transmit/receive data to/from an external controller (not shown); and a charging coil 36 for charging or recharging the IMD's battery 14 using an external charger, which is discussed in detail later.

FIG. 2 shows the IMD 10 in communication with an external charger 50 used to wirelessly convey power to the IMD 10, which power can be used to recharge the IMD's battery 14. The transfer of power from the external charger 50 is enabled by a primary charging coil 52. The external charger 50, like the IMD 10, also contains a PCB 54 on which electronic components 56 are placed. Some of these electronic components 56 are discussed subsequently. A user interface 58, including touchable buttons and perhaps a display and a speaker, allows a patient or clinician to operate the external charger 50. A battery 60 provides power for the external charger 50, which battery 60 may itself be rechargeable. The external charger 50 can also receive AC power from a wall plug. A hand-holdable housing 62 sized to fit a user's hand contains all of the components.

Power transmission from the external charger 50 to the IMD 10 occurs wirelessly and transcutaneously through a patient's tissue 25, via inductive coupling. FIG. 3 shows details of the circuitry used to implement such functionality. Primary charging coil 52 in the external charger 50 is energized via charging circuit 64 with an AC current, Icharge, to create a magnetic charging field 66. The charging circuit 64 may be controlled by the control circuitry 72 to maintain the current Icharge. The magnetic field 66 induces a current in the secondary charging coil 36 within the IMD 10, providing a voltage across coil 36 that is rectified (38) to DC levels and used to recharge the battery 14, perhaps via battery charging and protection circuitry 40 as shown. The frequency of the magnetic field 66 can be perhaps 80 kHz or so. When charging the battery 14 in this manner, it is typical that the housing 62 of the external charger 50 touches the patient's tissue 25, perhaps with a charger holding device or the patient's clothing intervening, although this is not strictly necessary.

The IMD 10 can also communicate data back to the external charger 50 during charging using reflected impedance modulation, which is sometimes known in the art as Load Shift Keying (LSK). This involves modulating the impedance of the charging coil 36 with data bits ("LSK data") provided by the IMD 10's control circuitry 42 to be serially transmitted from the IMD 10 to the external charger 50. For example, and depending on the logic state of a bit to be transmitted, the ends of the coil 36 can be selectively shorted to ground via transistors 44, or a transistor 46 in series with the coil 36 can be selectively open circuited, to modulate the coil 36's impedance. At the external charger 50, an LSK demodulator 68 determines whether a logic '0' or '1' has been transmitted by assessing the magnitude of AC voltage Vcoil that develops across the external charger's coil 52 in response to the charging current Icharge and the transmitted data, which data is then reported to the external charger's control circuitry 72 for analysis. Such back telemetry from the IMD 10 can provide useful data concerning charging to the external charger 50, such as the capacity of the IMD's battery 14, or whether charging of the battery 14 is complete and operation of the external charger 50 and the production of magnetic field 66 can cease. LSK communications are described further, for example, in U.S. Patent Application Publication 2013/0096652.

External charger 50 can also include one or more thermistors 71, which can be used to report the temperature (expressed as voltage Vtherm) of external charger 50 to its control circuitry 72, which can in turn control production of the magnetic field 66 such that the temperature remains within safe limits. See, e.g., U.S. Pat. No. 8,321,029, describing temperature control in an external charging device.

Vcoil across the external charger's charging coil 52 can also be assessed by alignment circuitry 70, which, although illustrated separately, can comprise part of the control circuitry 72, to determine how well the external charger 50 is aligned relative to the IMD 10. This is important, because if the external charger 50 is not well aligned to the IMD 10, the magnetic field 66 produced by the charging coil 52 will not efficiently be received by the charging coil 36 in the IMD 10. Efficiency in power transmission can be quantified as the "coupling" between the transmitting coil 52 and the receiving coil 36 (k, which ranges between 0 and 1), which generally speaking comprises the extent to which power expended at the transmitting coil 52 in the external charger 50 is received at the receiving coil 36 in the IMD 10. It is generally desired that the coupling between coils 52 and 36 be as high as possible: higher coupling results in faster charging of the IMD battery 14 with the least expenditure of power in the external charger 50. Poor coupling is disfavored, as this will require high power drain (e.g., a high Icharge) in the external charger 50 to adequately charge the IMD battery 14. The use of high power depletes the battery 60 in the external charger 50, and more importantly can cause the external charger 50 to heat up, and possibly burn or injure the patient.

Generally speaking, if the external charger 50 is well aligned with the IMD 10, then Vcoil will drop as the charging circuitry 64 provides the charging current Icharge to the charging coil 52. Accordingly, alignment circuitry 70 can compare Vcoil, preferably after it is rectified 76 to a DC voltage, to an alignment threshold, Vt. If Vcoil<Vt, then external charger 50 considers itself to be in good alignment with the underlying IMD 10. If Vcoil>Vt, then the external charger 50 will consider itself to be out of alignment, and can indicate that fact to the patient so that the patient can attempt to move the charger 50 into better alignment. For example, the user interface 58 of the charger 50 can include an alignment indicator 74. The alignment indicator 74 may comprise a speaker (not shown), which can "beep" at the patient when misalignment is detected. Alignment indicator 74 can also or alternatively include one or more Light Emitting Diodes (LED(s); not shown), which may similarly indicate misalignment.

BRIEF DESCRIPTION OF THE DRAWINGS

FIGS. 6A-6C show the non-uniformity of the magnetic field generated by a traditional mechanically-wound coil, in accordance with the prior art.

FIG. 7 illustrates the use of coupling to infer alignment, in accordance with the prior art.

FIG. 11 shows an isometric view of a split coil with portions on either side of a substrate, in accordance with an example of the invention.

FIG. 12 shows a cross-sectional view of the split coil that illustrates the flow of current through the coil's portions, in accordance with an example of the invention.

FIGS. 13A-13E show the use of the split coil with various sense coil arrangements, in accordance with different examples of the invention.

FIGS. 14A-14C show different views of a charging system that incorporates a split coil, in accordance with an example of the invention.

DETAILED DESCRIPTION

Figure 1A:
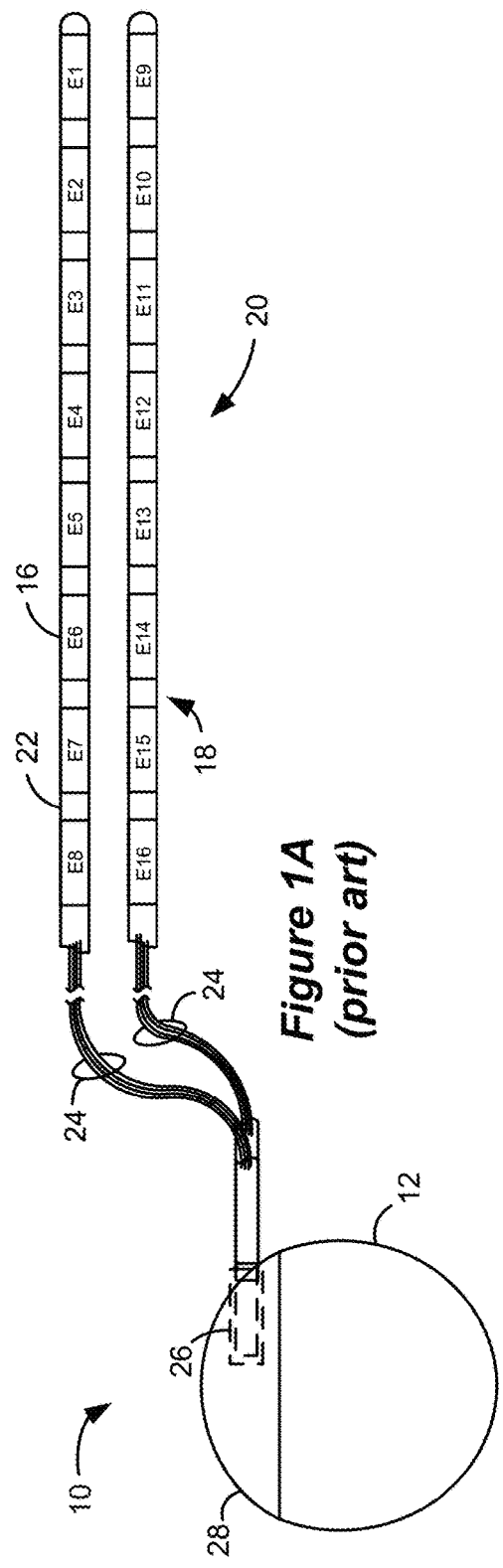
FIGS. 1A-1C show different views of an implantable pulse generator, a type of implantable medical device (IMD), in accordance with the prior art.
Figure 1C:
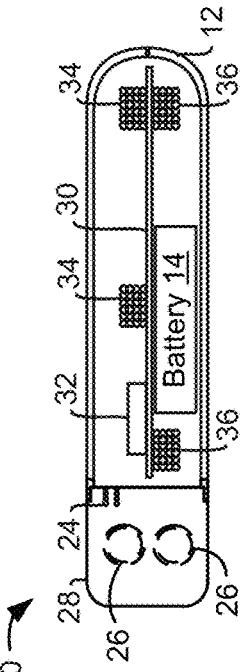
Figure 1B:
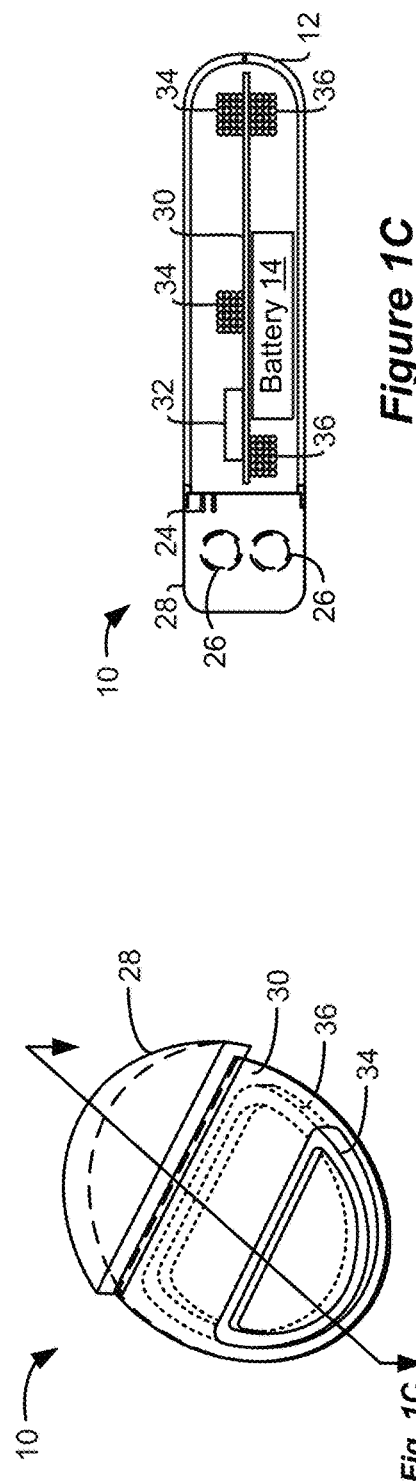
Figure 2:
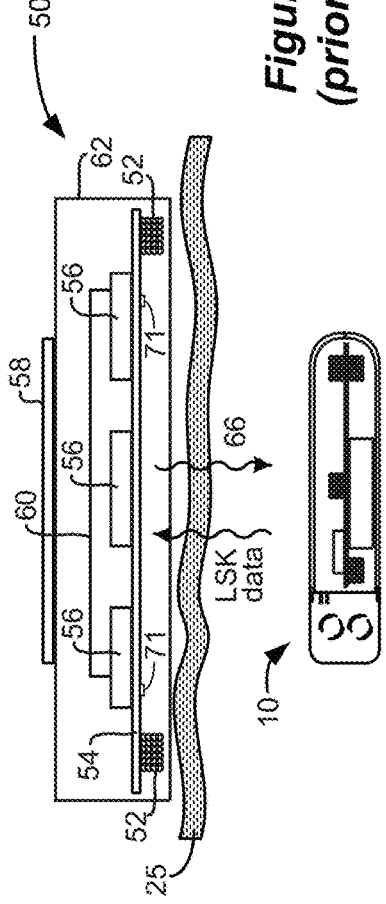
FIG. 2 shows an external charger being used to charge a battery in an IMD, in accordance with the prior art.
Figure 3:
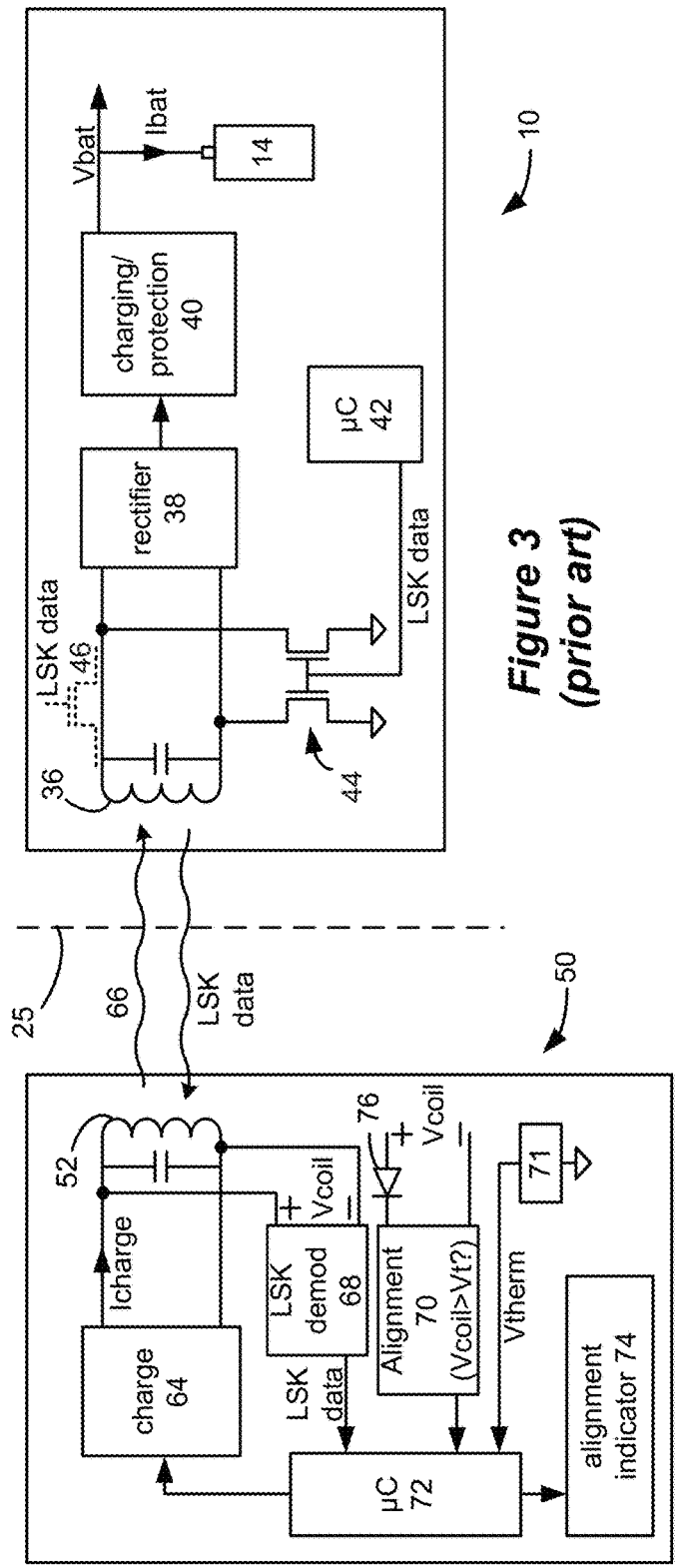
FIG. 3 shows circuitry in an external charger and an IMD, in accordance with the prior art.
Figure 4:
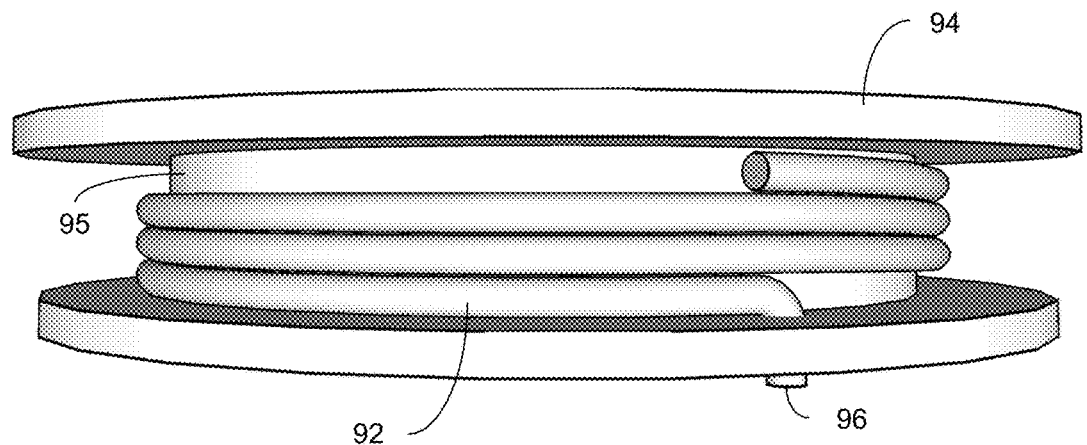
FIG. 4 shows a traditional method for creating a mechanically-wound coil, in accordance with the prior art.
Figure 5:
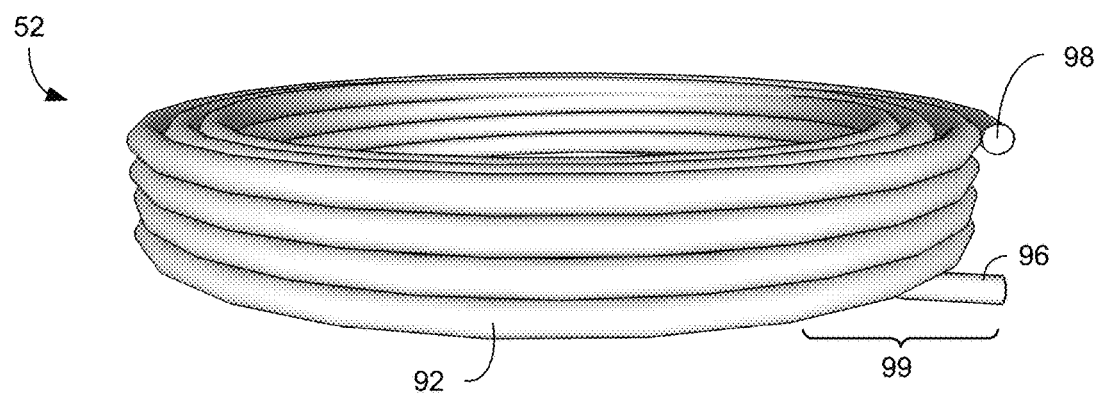
FIG. 5 shows a traditional mechanically-wound coil, in accordance with the prior art.

The inventor has identified a flaw in the use of coupling as a mechanism for determining alignment between an external charger and an IMD 10. The flaw is based on the manner in which coils such as the charging coil 52 are constructed, which, as illustrated in FIG. 4, involves winding an insulated conductor 92 around a bobbin 94. In a typical configuration, the conductor 92 is wound around the bobbin 94 to create several layers of turns. For example, a first layer of turns is wound against an interior surface 95 of the bobbin 94, a second layer of turns is wound against the first layer, and so on. When the coil 52 has been wound the desired number of turns, it is removed from the bobbin 94. In order to connect the coil 52 to the desired circuitry (e.g., charging circuitry 64 of FIG. 3), the ends 96 and 98 are electrically coupled to termination points (e.g., nodes of the PCB 54). However, because the ends 96 and 98 are separated by the layers of the coil 52, which can comprise a significant distance relative to the size of the coil 52, one of the ends must be routed radially across the layers. For example, as shown in FIG. 5, a portion 99 of the interior end 96 of the conductor 92 is routed to the exterior of the coil 52. Alternatively, a portion of the exterior end 98 of the conductor 92 may be routed to the interior of the coil 52. Thus, one of the ends of the conductor must be routed in a radial direction with respect to the coil 52. Because the coil 52 need not be circular, "radial" as used in this context refers to the routing of the conductor in the plane of the coil 92 and in a direction that is towards or away from the center of the coil 52.

In either case, the creation of a current-carrying path that is routed in a radial direction with respect to the coil 52 results in the generation of a non-uniform magnetic field. This effect is illustrated in FIGS. 6A-6C. When a current Icharge flows through the coil 52 in the direction shown in FIG. 6A, the magnetic field 66 is generated. The direction of the magnetic field 66 is into the page inside the area of the coil 52 and out of the page outside the area of the coil 52 as indicated by the "X" and "•" symbols, a notation that is adopted throughout this specification for illustrating the directionality of currents and magnetic fields into and out of the plane of the drawing page.

As shown in the side view of the coil 52 in FIG. 6B, however, the magnetic field 66' that is generated as a result of the current Icharge flowing through the portion 99 is in opposite directions on either side of a line 97. Therefore, the magnetic field 66' is in the same direction as the overall magnetic field 66 on one side of the line 97 and in the opposite direction of the overall magnetic field 66 on the other side of the line 97. As a result, the magnetic field 66 is weaker than the average field strength on one side of the line 97 and stronger than the average field strength on the other side of the line 97. This is illustrated by the size of the magnetic field symbols in FIG. 6A, which show that the magnetic field 66 is generally uniform but that there is a large difference in the field strength particularly near the edge of the coil 52 on either side of the portion 99 as a result of the contribution of the magnetic field 66'. The cross-sectional view of the coil 52 in FIG. 6C further illustrates the variance in the concentration of magnetic flux on different sides of the line 97. It will be appreciated that when the current direction is reversed, the same effect is observed. Specifically, when the direction of the current is reversed, the direction of the magnetic fields 66 and 66' are also reversed. As a result, regardless of the direction of the magnetic field 66, it is always stronger on the same side of the line 97.

Determining alignment based on the magnetic coupling between the charging coil 52 (shown as a single line that can represent the inside, outside, or average radius in FIG. 7 for simplicity) and the IMD 10 relies on the principle that the voltage Vcoil that is developed across the coil 52 to maintain the current Icharge can be expressed as a function of the radial offset r between the center of the coil 52 (ccoil) and the center of the IMD 10. The graph in FIG. 7 shows an ideal relationship between Vcoil and radial offset. Vcoil, like the magnetic field 66, is AC in nature, but it can be discussed and is graphed in FIG. 7 in terms of its magnitude, such as its rms, zero-to-peak, or peak-to-peak value. The ideal relationship depicted in FIG. 7 shows that as radial offset increases from a perfectly centered condition (r=0), Vcoil stays generally constant so long as the IMD 10 is within the area of the coil 52 (0<r<ra). When the radial offset increases such that a portion of the IMD 10 breaches the coil 52 (r=ra), Vcoil begins to increase. This increase is shown linearly in FIG. 7 for simplicity, but may be otherwise. As the radial offset increases further, the IMD 10 will eventually be fully outside of the coil 52 (r=rb), at which point Vcoil will be maximized and again constant, as it will be unaffected by the IMD 10.

The alignment threshold, Vt, is chosen from the ideal relationship between Vcoil and radial offset r. In the example shown, Vt is selected at the radial offset at which the IMD 10 is roughly half inside and half outside of the coil 52 (r=rt) and the corresponding Vcoil is roughly in the middle of its minimum and maximum values. This is just an example however as to how the alignment threshold can be chosen, and experimentation and simulation can dictate choosing Vt in different manners. For example, the threshold voltage illustrated in FIG. 7 may result in the IMD's charging coil 36 receiving too little of the magnetic field 66 as a practical matter. If so, a lower value for Vt could be chosen which would indicate misalignment at a smaller radial offset. Moreover, Vt may be affected by the depth at which the IMD 10 is actually implanted within a patient. For example, the dashed lines in FIG. 7 illustrate the ideal relationship between Vcoil and radial offset for shallower and deeper implant depths than the medium depth indicated by the solid line. Thus, Vt can be increased or decreased as necessary to account for these patient-specific parameters. Once a suitable alignment threshold is determined, it may be used by alignment circuitry 70 to determine and indicate misalignment to the patient as described above.

Figure 8:
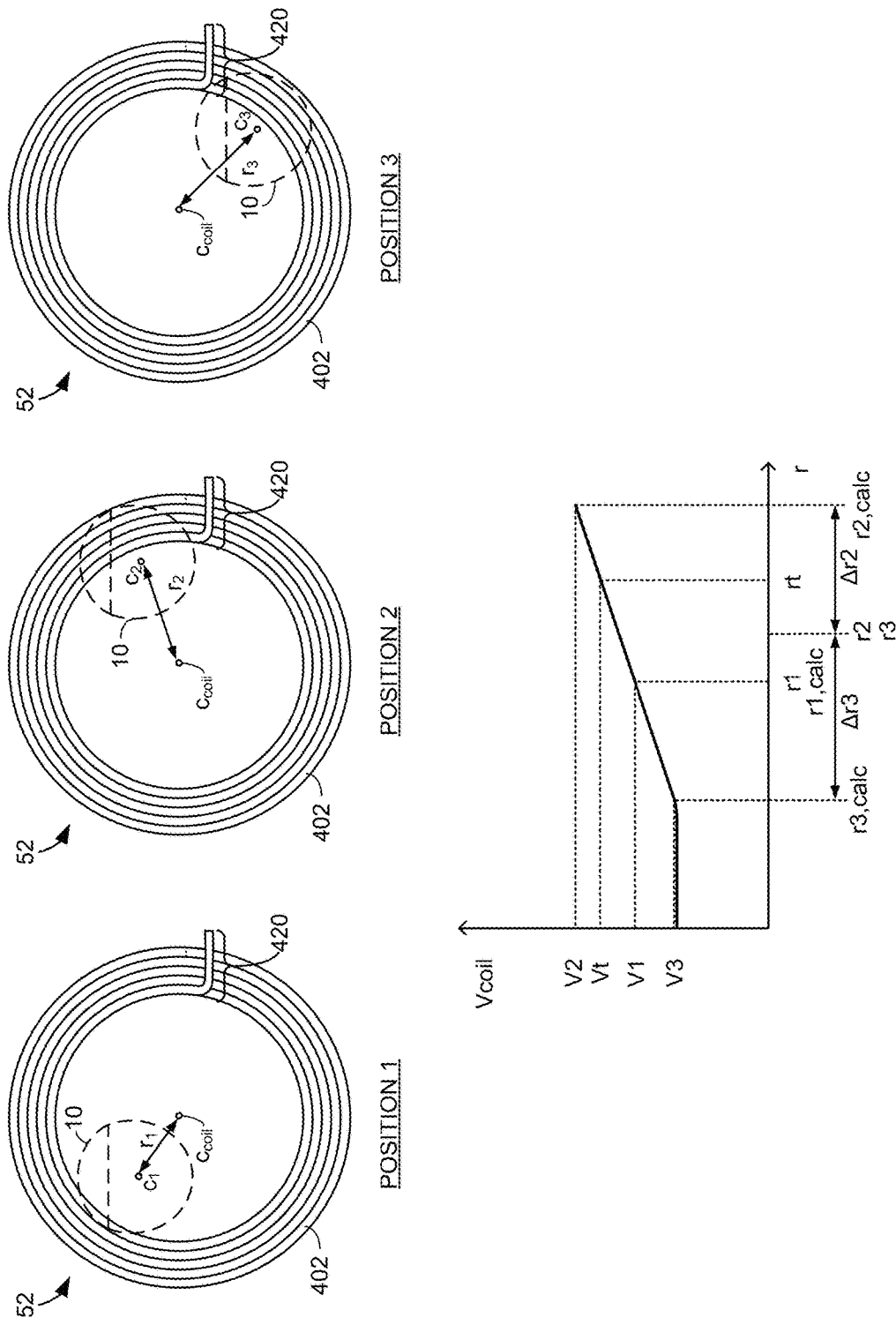
FIG. 8 illustrates errors that arise in the determination of alignment based on coupling for traditional mechanically-wound coils, in accordance with the prior art.

However, because the selection of the threshold voltage and the comparison of Vcoil to the selected threshold voltage are based on an ideal relationship between Vcoil and radial offset that assumes a uniform magnetic field, the non-uniformity of the magnetic field 66 can result in an inaccurate indication of alignment. The impact of the non-uniformity on alignment determination is illustrated in FIG. 8, which shows the IMD 10 at three different positions relative to the coil 52. In the first position, the center of the IMD 10 (c1) is located at a radial offset r1 from the center of the coil, in the second position, the center of the IMD 10 (c2) is located at a radial offset r2 from the center of the coil, and in the third position, the center of the IMD 10 (c3) is located at a radial offset r3 from the center of the coil. The distance r1 is less than the distances r2 and r3, which distances are equal and less than the threshold radial offset rt. Thus, of the three positions, the IMD 10 is most closely aligned with the coil 52 in the first position.

In the first position, the IMD 10 is located within a region of the coil 52 in which the magnetic field 66 is substantially unaffected by the contribution of the magnetic field 66' (see FIGS. 6A-6C). Therefore, the strength of the magnetic field 66 is as expected by the ideal relationship and the voltage required to maintain Icharge (V1) is an accurate indicator of the radial offset r1. This is illustrated in the chart in FIG. 8, which shows that the radial offset calculated based on V1 (r1,calc) corresponds with the actual value of the radial offset r1. In the second position, however, the IMD 10 is located within a region of the coil 52 in which the magnetic field 66 is significantly weakened by the contribution of the magnetic field 66' (see FIGS. 6A-6C). As a result, the coupling between the IMD 10 and the coil 52 is lower and the voltage required to maintain Icharge (V2) is higher than expected based on the ideal relationship. As shown in the chart in FIG. 8, the voltage (V2) corresponds to a radial offset (r2,calc) that is greater than the actual radial offset r2 by a distance of Δr2. Although r2 is less than the threshold radius (rt), because the voltage V2 exceeds the threshold voltage (Vt), the alignment circuitry 70 incorrectly identifies a misalignment condition and indicates such misalignment to the patient via the indicator 74 as described above. By contrast, in the third position, the IMD 10 is located within a region of the coil 52 in which the magnetic field 66 is significantly strengthened by the contribution of the magnetic field 66' (see FIGS. 6A-6C). As a result, the coupling between the IMD 10 and the coil 52 is higher and the voltage required to maintain Icharge (V3) is lower than expected based on the ideal relationship. As shown in the chart in FIG. 8, the voltage (V3) corresponds to a radial offset (r3,calc) that is less than the actual radial offset r3 by a distance of Δr3. Therefore, although the radial offset r3 exceeds the radial offset r1, the alignment circuitry 70 considers the IMD 10 to be in better alignment in the third position than in the first position. Moreover, although the radial offset r3 is equal to the radial offset r2, the alignment circuitry 70 identifies an alignment condition in the third position and a misalignment condition in the second position.

While the second position provides an example of a misalignment condition that can be indicated where the radial offset is less than the threshold rt, the opposite is also a concern. For example, if the IMD 10 is located at a radial offset that exceeds the threshold rt but in an area in which the magnetic field 66 is strengthened by the contribution of the magnetic field 66', the alignment circuitry 70 may indicate an alignment condition.

While the alignment circuitry 70 accurately indicates the degree of coupling and thus the amount of energy that is transferred from the charger 50 to the IMD 10 for a given positioning of the charger 50 relative to the IMD 10, inferring alignment from this information can be frustrating for the patient. For example, because the coupling information is presented to a patient as an indication of alignment, it can be difficult for the patient to understand how to position the charger 50, especially when the charger 50 is positioned such that the IMD 10 is located in an area that is affected by the contribution of the magnetic field 66', where small movements of the charger 50 cause changes in the indicated alignment position.

Figure 9:
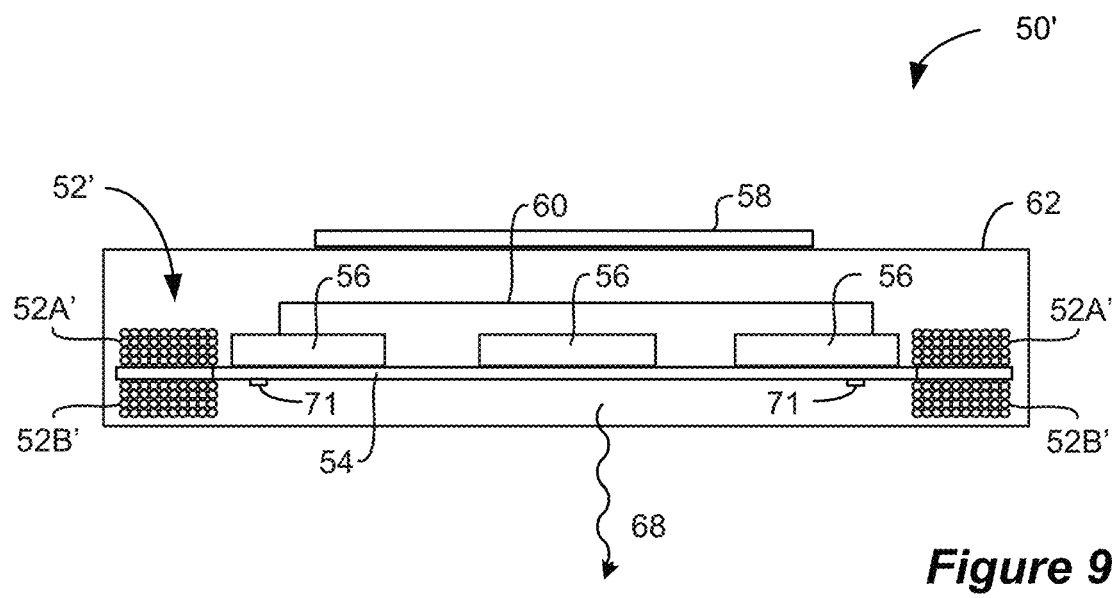
FIG. 9 shows a cross-sectional view of a modified external charger that includes a split coil, in accordance with an example of the invention.

The inventor has therefore conceived of an improved coil design that does not include a current-carrying portion that is routed radially with respect to the coil. FIG. 9 is a cross-sectional view of a modified charger 50' that incorporates a split charging coil 52', which includes coil portions 52A' and 52B' that are positioned on the top and bottom, respectively, of the PCB 54. In the example shown, the two portions 52A' and 52B' are identical in construction and therefore each includes one half of the total number of turns of the coil 52'. It is not required, however, that the coil portions be identical and there may be design reasons (e.g., space requirements) to construct a split coil having portions with different properties such as different numbers of turns, layers, etc. Moreover, while the coil 52' (and its portions 52A' and 52B') are illustrated as being circular in shape, a split coil can also take shapes other than circular (e.g., square, rectangular, or other shapes).

Figure 10:
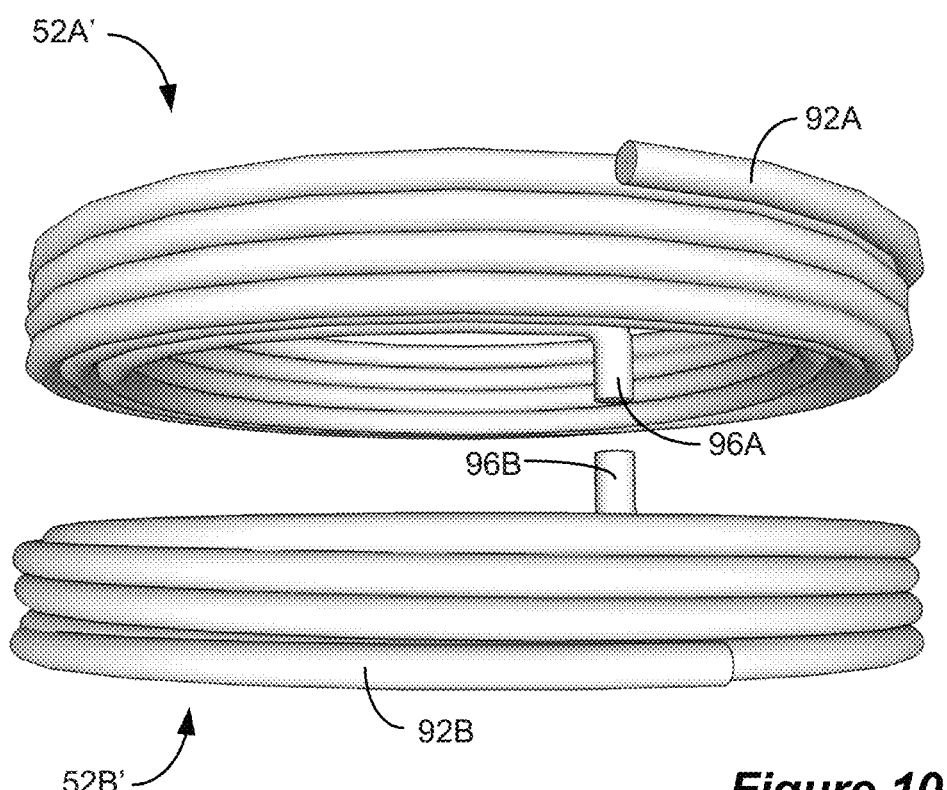
FIG. 10 shows an isometric view of the different portions of a split coil, in accordance with an example of the invention.

FIG. 10 is an isometric view of a portion of the coil portions 52A' and 52B' (several layers have been removed for purposes of clarity) with all other components of the charger 50' removed. Each of the portions 52A' and 52B' are preferably mechanically-wound coils that are created in the same manner as described above. Mechanically-wound in this context refers to the construction of a coil from a wound insulated conductor. Thus, each coil portion 52A' and 52B' is preferably created by winding an insulated conductor 92 around a bobbin to achieve the desired properties of the particular portions and the coil 52'. As will be understood, the type of conductor 92 that is appropriate for each portion 52A' and 52B' can be selected on the basis of the specific design parameters (e.g., current requirements, turn radius, voltage range, etc.). For example, the conductors 92A and 92B may include solid or stranded wires of varying numbers and sizes with different types of insulation to meet the design parameters. Similarly, the properties of each of the portions 52A' and 52B' (e.g., number of turns, number of layers, etc.) can be selected to obtain the desired properties of the coil 52'. As shown below, the interior ends 96 of the conductors 92 for each portion 52A' and 52B' are eventually electrically coupled to each other such that the portions 52A' and 52B' are connected in series to form the coil 52'.

FIG. 11 shows an isometric view of the partial coil portions 52A' and 52B' of FIG. 10 mounted on the top and bottom, respectively, of the PCB 54 (with other board-mounted elements removed). Attachment of the coil portions 52A' and 52B' to the PCB 54 (or other similar substrate) may be accomplished using known techniques. For example, the coil portions 52A' and 52B' may each be epoxied to the PCB 54 to fix the positions and shape of the coil portions 52A' and 52B'.

As shown in the cross-sectional view in FIG. 12, in a preferred arrangement, the coil portions 52A' and 52B' are aligned such that the interior ends 96A and 96B are directly aligned with each other (e.g., directly opposite the PCB 54 from each other). In this way, the ends 96 can be routed orthogonal to the plane of the PCB 54 such that they have no radial component. It will be understood that current flowing through a path that is orthogonal to the plane of the substrate (and the coil portions 52A' and 52B') will have little or no impact on the magnetic field generated by the coil 52'. In the embodiment illustrated in FIG. 11, the interior ends 96A and 96B are electrically coupled to each other through a via 78. The exterior ends 98A and 98B are electrically coupled to circuitry that drives the coil 52', such as charging circuitry 64. In the example shown, this is accomplished through the connection of the exterior ends 98A and 98B to contacts 80A and 80B, which contacts are, in turn, connected to circuitry that drives the coil 52', although other methods of connection are also possible. The coil portions 52A' and 52B' are oriented such that current flows in the same direction through each so that the magnetic fields generated by each portion have the same directionality. In the example shown, current flows out of the plane of the page on the right side and into the plane of the page on the left side (i.e., clockwise through both portions 52A' and 52B' when viewed from above). It will be noted, however, that current flows from the exterior to the interior in the portion 52A' and from the interior to the exterior in the portion 52B'. While positioning the coil portions 52A' and 52B' on opposite sides of a substrate such as PCB 54 provides a convenient means for electrically connecting the interior ends 96 to each other and the exterior ends 98 to drive circuitry, it is not strictly necessary that the portions be positioned on opposite sides of a substrate and other arrangements are possible.

Because the coil 52' does not include any current-carrying path that is routed radially with respect to the coil, the magnetic field 68 generated by the coil 52' is devoid of the non-uniformities of the magnetic field 66. As a result, a relationship between Vcoil and radial offset can be derived that is an accurate representation of alignment between the charging coil 52' and the IMD 10. Therefore, although the circuitry in the modified charger 50' otherwise operates in the same manner as the circuitry in the charger 50, the charger 50' provides a more accurate indication of alignment due to its inclusion of the split coil 52'.

While the determination of alignment has thus far been described in the context of the evaluation of Vcoil, alignment can also be determined based on the degree of coupling between a charger's charging coil and one or more separate sense coils. As described below, the charger 50' can therefore include modified alignment circuitry that evaluates signals (e.g., voltage or some other electrical parameter) from one or more alignment sense coils as opposed to the voltage Vcoil of the charging coil 52' to determine alignment. Because this type of an arrangement is also based upon coupling, it is similarly affected by a non-uniform field and therefore benefits from the use of a split coil such as the split charging coil 52'.

As illustrated in FIG. 13A, alignment is determined using measurements taken from sense coil 128, of which there is only one in the illustrated example. The single alignment sense coil 128 is circular, and comprises a radius ra as measured from the center of the charging coil 52'. As described above, the charging coil 52' is likewise circular and is depicted for simplicity as just a single circle. In the embodiment shown in FIG. 13A, radius ra is slightly smaller than the radius of the charging coil 52'. However, this is not strictly necessary. Radius ra may also equal or even exceed the radius of the charging coil 52'. Further, charging and sense coils can take shapes other than circular (e.g., square, rectangular, or other shapes). Note that even non-circular coils can be concentric (share the same center) even if not circular.

The alignment sense coil 128 (as well as the alignment sense coils described in the additional arrangements below) is preferably formed as a conductive trace in a circuit board such as PCB 54. However, this is not strictly necessary and the sense coil 128 can be formed as a wound conductor. In fact, the sense coil 128 can even be formed as a split coil such as the charging coil 52', although this is not necessary.

As the charging coil 52' produces the magnetic field 68, some amount of the magnetic field will couple to the alignment sense coil 128, with the degree of coupling being affected by how well the IMD 10 is aligned. Coupling causes a voltage Va to be formed across the alignment sense coil 128, which voltage is similarly related to radial offset of the IMD as is the voltage Vcoil. That is, the voltage Va is smallest when the IMD 10 is positioned entirely within the area of the sense coil 128 and increases as the IMD 10 breaches the area of the sense coil 128 to a maximum when the IMD 10 is fully outside of the sense coil 128 and does not affect the coupling between the charging coil 52' and the sense coil 128. The magnitude of Va can be tailored by appropriate design of the alignment sense coil 128. In this regard, note that Vcoil can range between +/−50V or so. Va by contrast preferably varies in a range that is able to be handled by the sensing electronics (e.g., alignment circuitry). For example, Va may preferably be set to vary between +/−3V. Setting Va can be achieved by varying the proximity of the alignment sense coil 128 to the primary coil 126. Va can also be set by engineering the number of turns that form the alignment sense coil 128 (e.g., the conductive traces in the circuit board from which alignment sense coil 128 is built). Likewise, the thickness and/or width of the traces of alignment sense coil 128 can be varied. Note that while sense coil 128 appears to comprise only a single trace comprising a single turn in the figures for simplicity, the reality might be otherwise, and instead a multi-turn sense coil 128 can be formed in either single-level or multi-level trace circuit boards.

FIGS. 13B-13E illustrate sense coil arrangements that can be utilized to determine a directionality of misalignment. For example, FIG. 13B includes two alignment sense coils 128a and 128b across which voltages Vaa and Vab can be induced. In the example shown, the alignment sense coils 128a and 128b comprise edge detection coils. The sense coils 128a and 128b each cover roughly half of the circumference of the charging coil 52', as shown by areas A and B. If the charging coil 52' shifts such that the IMD 10 (not shown) eclipses area A of sense coils 128a, then its voltage Vaa will drop. The alignment circuitry would thus understand that the charger 50' should be moved downwards to be in better alignment with the IMD 10. Likewise, if the IMD 10 eclipses area B of sense coil 128b, then Vab will drop, indicating that the charger 50' should be moved upwards. The direction of misalignment, or more preferably the direction of movement necessary to fix alignment, can be indicated by the user interface of the charger 50', and U.S. Pat. No. 8,473,066 discusses various means of indication, including direction-indicating LEDs that can be illuminated on the housing 62.

FIG. 13C is similar to FIG. 13B, but increases the areas A and B encompassed by alignment sense coils 128a and 128b, with each coil essentially covering a semicircle. In this example, induced voltage Vaa and Vab can both be used to determine a misalignment direction. For example, if Vaa drops relatively far in value from its maximum value, while Vab only drops a small amount, that would indicate that the IMD 10 is eclipsing area A to a great extent, but eclipsing area B to only a small extent. Thus, the charger 50' could indicate in this example that it should be moved upward to better align or center the assembly with the IMD 10.

FIG. 13D is similar to FIG. 13C, but connects the two sense coils together to form a single differential sense coil 128. In this instance, the direction of misalignment or non-centering would be indicated by the polarity of induced voltage Va. If Va is negative, the IMD 10 would largely be eclipsing area A, while if Va is positive, it would largely be eclipsing area B. If Va=0, this would indicate that the charging coil 52' and IMD 10 are perfectly aligned.

FIG. 13E includes sense coils 128a-d that are similar to those in FIG. 13B, but there are more than two, with each covering roughly a quarter of the circumference of the charging coil 52', as shown by areas A-D. This provides directionality information along orthogonal axes, thus allowing the charging system to not only determine whether the charging coil 126 is misaligned in the up/down direction, but in a left/right direction as well.

The adverse effects of magnetic field non-uniformity described above are exacerbated in the context of sense coil arrangements that are designed for the determination of the directionality of misalignment (such as those in FIGS. 13B-13E). This is because the determination of directionality of misalignment relies upon the coupling between the sense coil and the charging coil within a particular region of the charging coil (as opposed to the whole of the charging coil). Because the deviation in the strength of the magnetic field may affect different regions of the charging coil differently, the impact of such deviation may be focused in one or more sense coil regions. For example, if the sense coil arrangement depicted in FIG. 13E were used with a prior art charging coil 52, the strength of the magnetic field 66 would differ greatly within the areas A and D encompassed by coils 128a and 128d (see FIGS. 6A-6C), respectively, which would render the sense coil arrangement unusable for determining misalignment direction. Therefore, the use of a coil such as the split coil 52' is even more crucial where measurements of coupling within a partial region of the charging coil are utilized. The use of sense coils for the determination of alignment between an external charger and an IMD 10 is further described in U.S. Application Ser. No. 62/350,451, filed Jun. 15, 2016, which is incorporated herein by reference in its entirety.

While the external charger has to this point been described as a device contained within a single housing, FIG. 14 illustrates a charging system 100 in which an electronics module 104 is separated from a charging coil assembly 102. The electronics module 104 and the charging coil assembly 102 are connected by a cable 106. The cable 106 may be separable from both the electronics module 104 and the charging coil assembly 102 via a port/connector arrangement, but as illustrated cable 106 is permanently affixed to the charging coil assembly 102. The other end of the cable 106 includes a connector 108 that can attach to and detach from a port 122 of the electronics module 104.

Electronics module 104 preferably includes within its housing 105 a battery 110 and active circuitry 112 needed for charging system operation. Electronics module 104 may further include a port 114 (e.g., a USB port) to allow its battery 110 to be recharged in conventional fashion, and/or to allow data to be read from or programmed into the electronics module, such as new operating software. Housing 105 may also carry a user interface, which as shown in the side view of FIG. 14B can include an on/off switch to begin/terminate generation of the magnetic field 90, and one or more LEDs 118a and 118b. In one example, LED 118a is used to indicate the power status of the electronics module 104. For example, LED 118a may be lit when its battery 110 is charged, and may blink to indicate that the battery 110 needs charging. LED 118*b* may operate to provide an indication of alignment of the charging coil assembly 102 with the IMD 10. More complicated user interfaces, such as those incorporating a speaker and a display, could also be used. User interface elements can be included on other faces of the electronic module's housing 105, and may be placed such that they are easily viewed for the therapeutic application at hand (e.g., SCS, DBS). Electronics are integrated within the housing 105 of the electronics module 104 by a circuit board 120.

Charging coil assembly 102 preferably contains only passive electronic components that are stimulated or read by active circuitry 112 within the electronics module 104. Such components include the primary charging coil 126, which as illustrated comprises a split coil that includes two wound conductor coil portions 126A and 126B that are mounted on the top and bottom of the circuit board 124 within the charging coil assembly 102, which circuit board 124 is used to integrate the electronic components within the charging coil assembly 102. The charging coil 126 is energized by charging circuitry 64 (FIG. 15) in the electronics module 104 to create the magnetic charging field 90. Further included within the charging coil assembly 102 are one or more sense coils 128, which as shown in the cross section of FIG. 14B, are preferably formed using one or more traces in the PCB 124. While it is preferred that charging coil 126 comprise a wound conductor, and that the one or more sense coils comprise traces within the circuit board 124, this is not strictly necessary: the charging coil 126 can also be formed from circuit board traces (e.g., traces in separate layers of the PCB 124 to eliminate any radial current-carrying path), and the one or more sense coils can comprise one or more wound conductors. Note that the charging coil 126 and the one or more sense coils 128 are formed in planes that are parallel, and can also be formed in the same plane.

Further passive components preferably included within the charging coil assembly 102 include one or more tuning capacitors 131, which are utilized to tune the charging coil 126 to its resonant frequency (fres). Each of the one or more sense coils 128 may also be coupled to a tuning capacitor 131, although this is not necessary and is not shown in further circuit diagrams. The charging coil assembly 102 can further include one or more thermistors 136, which can be used to report the temperature of the charging coil assembly 102 to the electronics module 104. Such temperature data can in turn control production of the magnetic field such that the temperature remains within safe limits. See, e.g., U.S. Pat. No. 8,321,029, describing temperature control in an external charging device.

Components in the charging coil assembly 102 are integrated within a housing 125, which may be formed in different ways. In one example, the housing 125 may include top and bottom portions formed of hard plastic that can be screwed, snap fit, ultrasonic welded, or solvent bonded together. Alternatively, housing 125 may include one or more plastic materials that are molded over the electronics components.

Figure 15:
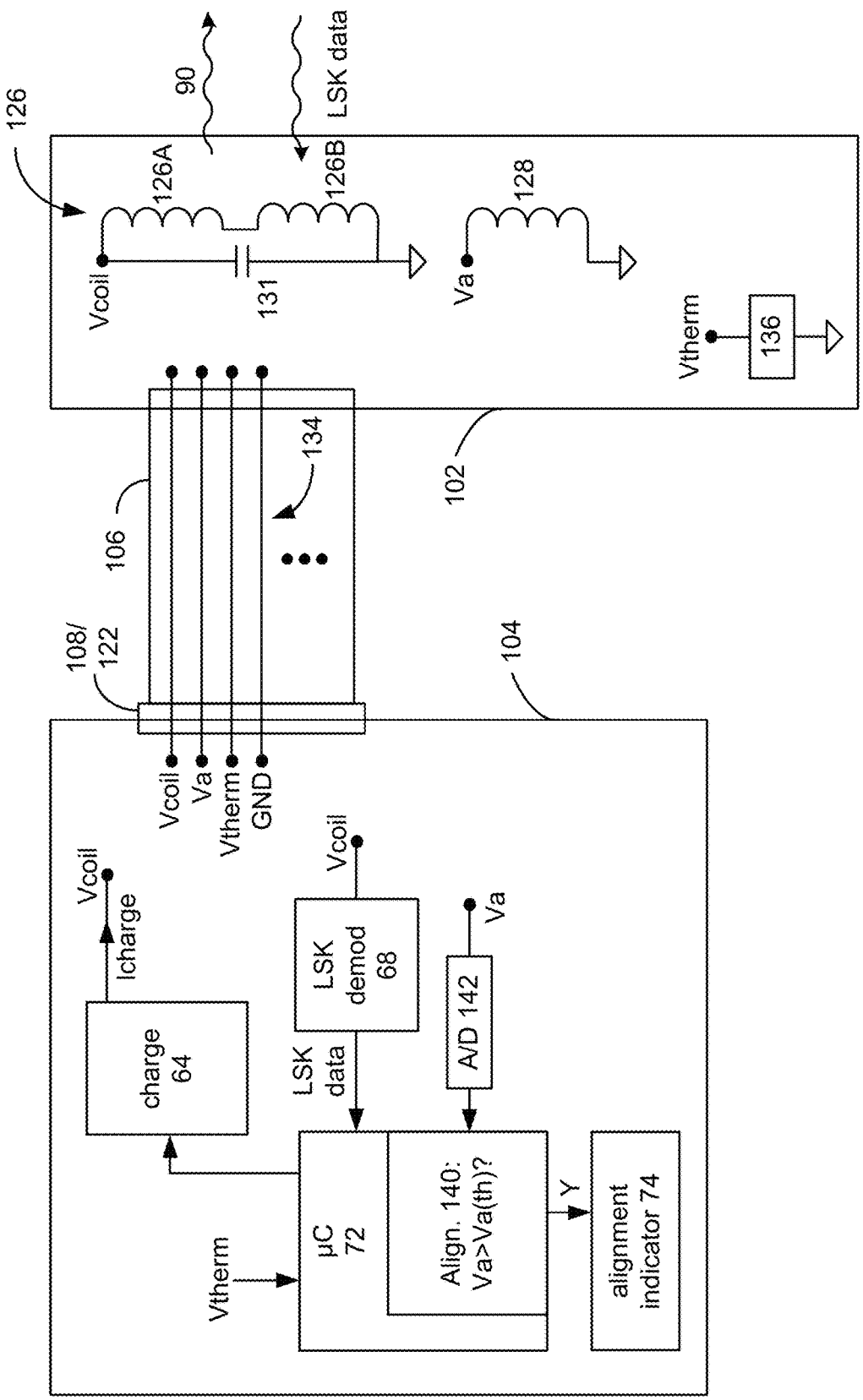
FIG. 15 shows circuitry of the charging system illustrated in FIGS. 14A-14C, in accordance with an example of the invention.

Like the external charger 50 described earlier (FIG. 3), the electronics module 104 may include (as part of circuitry 112; FIG. 15) control circuitry 72 that controls charging circuitry 64 to generate a charging current, Icharge. This current is passed via connector/port 108/122 through a wire 134 in cable 106 to energize the charging coil 126 to produce the magnetic field 90. The resulting voltage across the charging coil 126, Vcoil, perhaps as dropped in voltage using a voltage divider, can be monitored for LSK communication from the IMD 10 with the assistance of LSK demodulator 68. And again, one or more indications of temperature (Vtherm) can be reported from the one or more thermistors 136 in the charging coil assembly 102 to allow the control circuitry 72 to control production of the magnetic field 90 as mentioned previously. While it is preferable to place control circuitry 72 and other circuitry 112 aspects in the electronics module 104, this is not strictly necessary, and instead such components can reside in the charging coil assembly 102, for example, on its circuit board 124. Thus, electronics module 104 may retain only battery 110 and user interface aspects.

As described above, the split coil design reduces or eliminates current-carrying paths that are radial with respect to the coil. As a result, the split coil generates a uniform magnetic field that enables an accurate determination of alignment between a charger and an IMD based on coupling. While the split coil design has been described in the context of its use as a charging coil, it will be understood that coils designed for other uses may also benefit from the magnetic field uniformity of the split coil. For example, there may be reasons to employ a split coil design for the sense coils in an external charger, the charging coil in the IMD, or a telemetry coil in the IMD or other communicating device.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover equivalents that may fall within the spirit and scope of the present invention as defined by the claims.

What is claimed is:

1. An external charger for wirelessly providing power to an implantable medical device (IMD), comprising:
   a circuit board having a plane; and
   a charging coil configured to produce a magnetic field to provide power to the IMD, wherein the charging coil comprises a first mechanically-wound coil portion on a first side of the circuit board and a second mechanically-wound coil portion on a second side of the circuit board, wherein the first coil portion and the second coil portion are connected in series, and wherein the first and second coil portions are formed in planes parallel to the plane of the circuit board.

2. The external charger of claim 1, wherein an interior end of the first coil portion is connected to an interior end of the second coil portion.

3. The external charger of claim 2, wherein the interior end of the first coil portion and the interior end of the second coil portion are connected through a via in the circuit board.

4. The external charger of claim 1, further comprising alignment circuitry configured to measure one or more electrical parameters to determine a measure of alignment between the charging coil and the implantable medical device.

5. The external charger of claim 4, wherein the one or more electrical parameters comprise a voltage across the charging coil.

6. The external charger of claim 4, further comprising one or more sense coils.

7. The external charger of claim 6, wherein the one or more electrical parameters comprise a voltage across each of the one or more sense coils.

8. The external charger of claim 6, wherein the one or more sense coils are each formed as a trace in the circuit board.

9. The external charger of claim 6, wherein the alignment circuitry is configured to determine a direction of misalignment between the charging coil and the implantable medical device.

10. The external charger of claim 1, further comprising an electronics module and a charging coil assembly coupled to the electronics module by a cable,
wherein the charging coil and the circuit board are within the charging coil assembly, and
wherein the electronics module comprises charging circuitry configured to generate a charging current through the charging coil.

11. An external charger for providing power to an implantable medical device (IMD), comprising:
a substrate having a plane;
control circuitry mounted on the substrate; and
a charging coil configured to produce a magnetic field to provide power to the IMD, wherein the charging coil comprises a first portion comprising a first wound conductor on a first side of the substrate and a second portion comprising a second wound conductor on a second side of the substrate, wherein the first wound conductor is electrically connected to the second wound conductor, and wherein the first and second portions are formed in planes parallel to the plane of the circuit board.

12. The external charger of claim 11, wherein an interior end of the first wound conductor is connected to an interior end of the second wound conductor.

13. The external charger of claim 12, wherein the first portion and the second portion are positioned on the substrate such that the interior end of the first wound conductor is directly opposite the substrate of the interior end of the second wound conductor.

14. The external charger of claim 12, wherein the interior end of the first wound conductor is connected to the interior end of the second wound conductor through a via in the substrate.

15. The external charger of claim 11, wherein an exterior end of the first wound conductor is connected to a first contact on the substrate and an exterior end of the second wound conductor is connected to a second contact on the substrate, and wherein the first and second contacts are coupled to charge circuitry that is controlled by the control circuitry to deliver a charge current through the charging coil.

16. The external charger of claim 11, wherein the control circuitry comprises circuitry configured to evaluate one or more electrical parameters to determine a measure of alignment between the external charger and the IMD.

17. The external charger of claim 16, wherein the one or more electrical parameters comprise a voltage across the charging coil.

18. The external charger of claim 16, wherein the one or more electrical parameters comprise a voltage across one or more sense coils that are formed as traces on the substrate.

19. The external charger of claim 18, wherein the circuitry configured to determine the measure of alignment is configured to determine a direction of misalignment between the external charger and the implantable medical device.

20. The external charger of claim 11, further comprising an electronics module and a charging coil assembly coupled to the electronics module by a cable,
wherein the charging coil and the substrate are within the charging coil assembly, and
wherein the control circuitry is within the electronics module.

* * * * *